United States Patent [19]

Working

[11] Patent Number: 4,941,460
[45] Date of Patent: Jul. 17, 1990

[54] CARPAL BRACE

[76] Inventor: Loren Working, P.O. Box 147, Barberton, Ohio 44203

[21] Appl. No.: 431,687

[22] Filed: Nov. 3, 1989

Related U.S. Application Data

[63] Continuation of Ser. No. 208,773, Jun. 20, 1988, abandoned.

[51] Int. Cl.$^5$ .............................................. A61F 5/00
[52] U.S. Cl. .................................. 128/77; 128/89 R
[58] Field of Search .................... 128/77, 87 A, 87 R, 128/80 C, 88, 89 R, 68

[56] References Cited

U.S. PATENT DOCUMENTS

| | | | |
|---|---|---|---|
| 1,177,398 | 3/1916 | Dorang | 128/88 |
| 3,235,258 | 2/1966 | Stroburg | 128/88 |
| 3,776,225 | 12/1973 | Lonardo | 128/77 |
| 3,788,307 | 1/1974 | Kistner | 128/77 |
| 4,382,439 | 5/1983 | Shen | 128/77 |
| 4,441,490 | 4/1984 | Nirschl | 128/77 |
| 4,618,147 | 10/1986 | Hurd et al. | 128/88 |
| 4,666,158 | 5/1987 | Moro | 128/88 |
| 4,677,971 | 7/1987 | Lindemann | 128/88 |
| 4,716,892 | 1/1988 | Brunswick | 128/80 C |
| 4,840,168 | 6/1989 | Lonardo | 128/77 |

FOREIGN PATENT DOCUMENTS 3210838 10/1983 Fed. Rep. of Germany ........ 128/77

Primary Examiner—Edgar S. Burr
Assistant Examiner—Ren Yan
Attorney, Agent, or Firm—Oldham, & Oldham Co.

[57] ABSTRACT

An orthopedic brace is described which substantialy permits the full use of the fingers and the hand, while immobilizing the wrist for the purpose of preventing Carpal Tunnel Syndrome, or in the event the Syndrome is already present, for causing a remission and eventual elimination of the syndrome. The brace comprises a stiff member extending dorsally down the forearm with a moldable plastic crosspiece attached to the lower end thereof in a generally tee-shaped configuration. The crosspiece is elevated at an angle of about 7-10x from the horizontal to accommodate the normal dorsi flexion. The moldable plastic cross-piece is softened by warming to the degree necessary to mold it to the patient's hand. The brace is then placed on the upper, or dorsal surface of the wearer's forearm and hand and the softened crosspiece is molded to the contours of the back of the wearer's hand, and curled around the outside of the hand. The brace is thereafter fastened to the wearer by means of the cincture straps one of which passes across the palm, and the other two around the middle and upper parts of the forearm, none passing around the wrist. The immobility thus achieved precludes trauma within the carpal tunnel, preventing the syndrome, or if already present, it treats the syndrome through the prevention of further trauma by providing healing rest without subjecting the patient to a loss of normal hand activity.

8 Claims, 2 Drawing Sheets

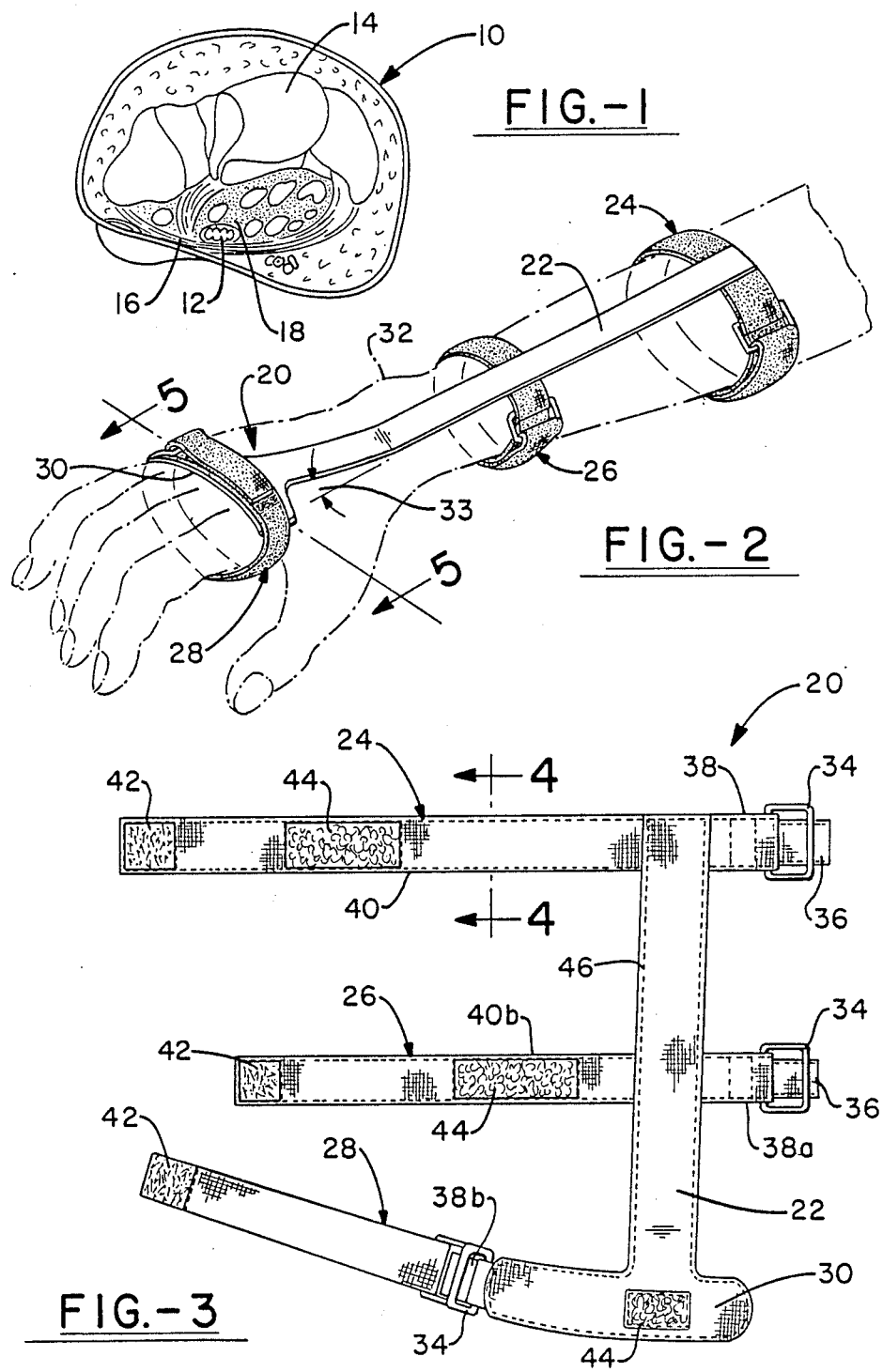

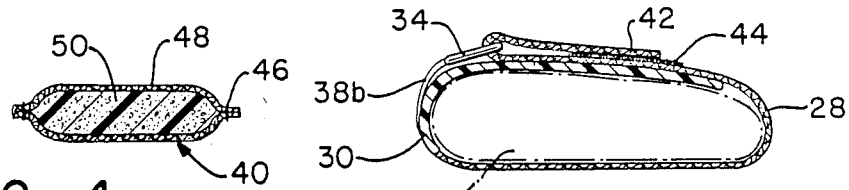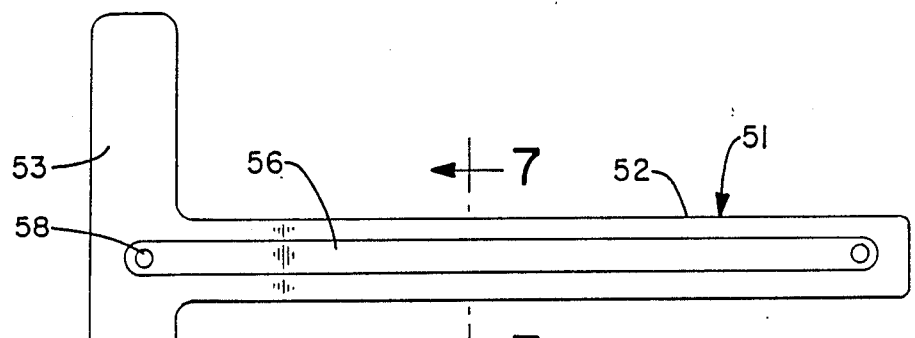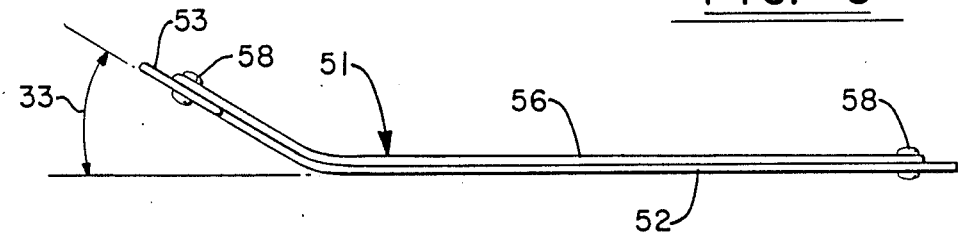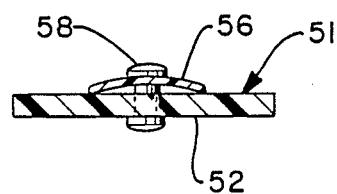

CARPAL BRACE

This is a continuation Ser. No. 07/208,773 filed on 6-20-88 now abandoned.

TECHNICAL FIELD

This invention relates to an orthopedic device. More particularly, this invention relates to an orthopedic device useful in the treatment of inflamed and swollen tissue associated with an individuals traumatized carpal tunnel. Specifically, this invention relates to a splint or brace device which can be fastened to a wearer's forearm and hand and is unique in that it prevents flexion, hyperextension and ulnar deviation of the wearer's wrist without interfering with the normal dexterity of the fingers and the whole hand, thereby avoiding the trauma responsible for Carpal Tunnel Syndrome. It is also useful in the treatment of the syndrome by preventing further trauma, thus allowing the body's natural healing processes to proceed.

BACKGROUND OF THE INVENTION

One of the commonest afflictions experienced by workers and other engaged in tasks or activities requiring repeated flexing of the wrist is the condition known as Carpal Tunnel Syndrome. The carpal tunnel is located in thewrist at the heel of the hand. In this tunnel, contained by a surrounding tough membrane, lie eight carpal bones, ten ligaments, the median nerve, and their attendant synovial tissues. Due to the nature of the components forming it, the carpal tunnel is tightly packed; consequently when tissues within the tunnel are irritated, (for example, when the tissues are irritated by highly repetitive wrist motions), the swollen tissues compress the median nerve causing the painful condition known as Carpal Tunnel Syndrome.

Carpal Tunnel Syndrome is also a fairly common disorder in women approaching middle age, there being some evidence that a change in the balance of female sex hormones can lead to an accumulation of fluid and a consequent swelling in their wrist at the time of menopause. This same condition may occur during pregnancy.

Irrespective of its cause, the symptoms of Carpal Tunnel Syndrome are a tingling and a numbness of the hand, often accompanied by pains that progress up the arm from the wrist. If steps are not taken to stop the progress of the syndrome once it starts, it can lead to serious injury to the median nerve and ultimately to the loss of function of the entire arm.

Treatments vary; the use of diuretics in the case of fluid buildup, the injection of steroid drugs, etc., and where the cause is highly repetitive wrist activity, such activity must be curtailed and the wrist splinted in such a way as to prevent flexion during the sleeping period. A frequent treatment involves surgery; freeing the compression by cutting through the tough membrane surrounding the tunnel, thus relieving the pressure on the median nerve. While this procedure gives immediate relief, such relief is most often temporary. Quite often the subsequent development of scar tissue exacerbates the original condition.

Another preferred method of alleviation is the application of a splint to prevent flexion of the wrist. In almost every instance, however, the splints in use today are splints that were designed for other specific purposes. While helpful, such splints do not provide the full treatment required by Carpal Tunnel Syndrome. They restrict finger and hand dexterity, apply external pressure on the median nerve over the carpal tunnel, and do not conform to the normal wrist configuration; namely the "dorsi-lift" so necessary to the natural healing process.

In view of the foregoing, therefore, it is a first aspect of the invention to provide the orthopedic device that prevents carpal tunnel syndrome.

A second aspect of this invention is to furnish an orthopedic device which gives relief from the pain of carpal tunnel syndrome.

A third aspect of the invention is the immobilization of the wrist for a period sufficient to allow natural body healing processes to restore the tissues in and around the carpal tunnel to their normal healthy condition.

An additional aspect of the invention is to provide a non-invasive method for treating the carpal tunnel syndrome disabilities, and without resort to the application of, or the taking of drugs.

A further aspect of this invention is the provision of a brace which is cinctured in such a fashion as to avoid any injurious or aggravating external pressure on the carpal tunnel.

A still further aspect of the invention is to permit a wearer to continue normal hand activities, substantially free from pain which would otherwise be experience.

Yet another aspect of the invention is the ability to support the wrist in a neutral position so that the natural body healing processes may take place while avoiding further injury to the carpal area.

These and other aspects of the invention are provided by a carpal brace intended for positioning on the dorsal surface of a wearer's hand and forearm comprising a spine portion with a crosspiece portion attached to an end thereof, said end and said crosspiece portion being inclined upwardly from the rest of said spine at an angle which conforms to the dorsi-lift of a wearer, said spine portion of said brace and being elevated to conform to the dorsi-lift of a wearer, said brace also including lower, middle and upper cincture straps, said lower cincture strap being connected to the crosspiece portion of said brace, and adapted to pass around the palm of the wearer's hand, thereby securing said crosspiece portion to the back of said hand, while said middle and upper straps are connected to, and located near the middle, and at the upper end, respectively, of the spine portion of said brace, being adapted to pass around the parts of the wearer's forearm to which they are adjacent, spaced apart from the wearer's wrists, so as to allow the securing of said spine portion to the top of the said forearm.

The foregoing and yet additional aspects of the invention are provided by the process of immobilizing the wrist of an individual comprising applying a thermoplastic brace to the dorsal surface of the individual's hand and forearm associated with said wrist, without applying external pressure to the carpal tunnel, said brace having a spine portion, with a crosspiece portion attached to an end thereof, said end and said crosspiece portion being inclined upward from the rest of said spine at an angle which conforms to the dorsi-lift of a wearer, said portions being joined in a generally tee-shaped configuration and securing said brace to said surface by bending one end of said crosspiece portion about the ulnar edge of said hand, and thereafter securing said brace firmly in place by fastening it to said hand and forearm by means of a plurality of cincture straps attached to said brace, all of said cincture straps being spaced apart from said wrist.

BRIEF DESCRIPTION OF THE DRAWINGS

The invention will be better understood when reference is had to the following drawings, in which like numbers refer to like parts.

FIG. 1 is a cross section of an individual's wrist showing anatomical details, including those associated with the carpal tunnel.

FIG. 2 is an isometric view of the carpal brace of the invention fastened to the hand and forearm of an individual.

FIG. 3 is a plan view of a carpal brace of the invention.

FIG. 4 is a cross section of a cincture strap along Line 4—4 of FIG. 3.

FIG. 5 is a cross section of the hand of an individual wearing a carpal brace of the invention, along Line 5—5 of FIG. 2.

FIG. 6 is a plan view of a carpal brace spine member with a rigidifying member riveted thereto.

FIG. 6A is a side elevation of the carpal brace spine member of FIG. 6.

FIG. 7 is a cross section of the carpal brace spine member of FIG. 6, along Line 7—7.

DETAILED DESCRIPTION OF THE INVENTION

FIG. 1 shows a cross section of the wrist, generally 10, showing details of the anatomical structure. In the Figure, the wrist bones or "carpals" 14, with the tough membrane 16 together form the parameter of the carpal tunnel. A median nerve 12 is located within the confines of the carpal tunnel, surrounded by soft tissue 18.

The median nerve 12 provides sensation to the palmar aspect of the thumb, index, middle and one half of the little finger. It enervates the muscles at the base of the thumb, allowing opposition of the thumb for pulp to pulp pinch to the other fingers.

It is the compression neuropathy of the median nerve 12 at the level of the wrist in this tight space which constitutes what is termed the carpel tunnel syndrome, a condition which if untreated produces an extremely limiting condition which can result in the effective loss of use of the hand. Any disorder or activity-related trauma that causes swelling of the soft synovial tissue relatively decreases the size of the canal and can lead to the disabling median nerve compression.

FIG. 2 provides an isometric view of a carpal brace, generally 20, in its position of use on an individual's forearm and hand. Essentially, the brace 20 accomplishes the primary function of immobilizing the wrist area 32 of the wearer. This prevents the trauma that causes the syndrome, and where the syndrome is already present, enables the natural healing processes of the body to reduce the swelling thus eliminating the carpal tunnel syndrome condition. Immobilization of the wearer's wrist is made possible due to inflexibility of the brace spine 22, which is fastened to the forearm by an upper forearm cincture, generally 24, a middle forearm cincture, generally 26, and by a palm cincture generally 28. The palm cincture 28 is anchored to a brace crosspiece 30, the latter being attached to the brace spine 22. Several unique features are provided by the carpal brace 20, including the fact that the middle forearm cincture 26 is spaced apart from the wrist area 32. The absence of a cincture about the wrist area 32 is important, since the presence of a cincture at the point of the wrist would result in pressure on the carpal tunnel; it would thus tend to create carpal tunnel syndrome, or if the syndrome were already present, would tend to exacerbate the condition. As will be seen from FIG. 2, attachment of the cincture 30 about the palm of the wearer's hand produces the desired wrist immobility, while at the same time leaving the wearer's fingers free to pursue useful flexion. Rather than having a disabled limb, therefore, the patient is able to retain the substantially normal use thereof without pain.

It has been found to be extremely beneficial to the rapid recovery of a patient afflicted with carpal tunnel syndrome if the position of the patient's hand and wrist, relative to the forearm, is normal. In a fully relaxed position, the back of the hand extending into the wrist forms an angle with the axis of the forearm which is known as the "dorsi-lift". The angularity of the dorsi-lift will vary somewhat, depending upon the anatomy of the individual. Consequently, it has been found to be important that an appropriate dorsi-lift angle 33 be provided adjacent the area of the brace spine 22 where the spine adjoins the brace crosspiece 30.

While reasonable latitude is permissible in locating cinctures, as stated, it is necessary to space the middle forearm cincture 26 apart from the wrist 32, and althoug the actual spacing will depend upon the anatomy of the brace wearer, in the case of an adult of normal proportions, it has been found necessary to allow a space of at least 2¼ inches between the middle forearm cincture 26, and the point at which the wrist joins the heel of the hand, i.e., the upper part of the hand. In the case of the upper forearm cincture 24, a location commonly about 3 inches below the elbow will be chosen.

FIG. 3 is a plan view of a carpal brace 20 of the invention As shown, the brace 20 comprises a brace spine 22, a part of which is the brace crosspiece 30 positioned at substantially right angles thereto, forming a generally tee-shaped structure. The spine 22 and crosspiece 30, are covered with a fabric material which may be held thereon by means of stitching 46. Attached to the spine member 22 are upper forearm cincture, generally 24, and middle forearm cincture, generally 26. The upper forearm cincture 24 comprises a tongue strap 40, and a buckle strap 38 to which is attached a buckle 34. A buckle pad 36 may also be attached to a buckle strap 38 to protect against painful pressure from the buckle 34 on the wearer's arm. In use, the tongue strap 40 is passed under the wearer's arm through the buckle 34, and the tongue strap is doubled back and a VELCRO hook pad 42 is engaged with a cooperating VELCRO loop pad 44, securing the cincture securely in place. While use of hook and loop fasteners of the VELCRO type, which are well known in the art are convenient, other fasteners such as snaps, hooks and eyes, or others, could also be employed for the purpose. Similarly tongue strap 40b of the middle forearm cincture 26 is passed through the buckle 34 of buckle strap 38a, doubled back and the VELCRO hook pad 42 is attached to the VELCRO loop pad 44. Again the pressure of the buckle 34 on the wearer's arm is avoided by the presence of a buckle pad 36. The palm cincture is structured somewhat differently than the other cinctures in that, as shown in FIG. 3, which illustrates a carpal brace 20 designed to be worn on the right arm, the cincture is shown attached to the ulnar side, i.e., the outside, of the crosspiece 30. From such a position it is passed under the palm, then through the buckle 34, and doubled back to the point at which the VELCRO hook pad 42 can be engaged with the VELCRO loop pad 44.

As previously stated, the dimensions of the carpal brace 20, and its components, may be varied within broad limits. Again, however, in the case of an adult, dimensions will commonly include an upper forearm cincture 24 having a width of about 1 inch to 1½ inches, and a length of from about 11 inches to 18 inches. The middle forearm cincture 26 will be somewhat smaller, being typically from about 1 inch to 1½ inches wide and from about 8 inches to 14 inches long. The brace spine 22 will conveniently be designed to be from about 1¼ inches to 1¾ inches wide, a width of about 1½ inches being typically preferred. The length of the spine 22 may conveniently be about 9 to 11 inches, about 9 inches being preferred. The cross member 30, will usually be selected to be from about 4 to 5 inches long, the ulnar portion constituting about 3 inches of such length. It has been found that a palm cincture 28 about 10 inches to a 12 inches long, with a width of about ½ inch to ¾ inch satisfactorily secures the cincture to the hand, but at the same time is small enough to provide adequate latitude of movement to the wearer's fingers for normal work functions. Buckle straps of from about 1 inch to 1½ inches in length are satisfactory.

FIG. 4 shows a typical cross section of a cincture strap, in the case of the Figure, along Line 4—4 of FIG. 3. In the Figure, the cincture strap comprises layers of outer fabric 48, surrounding padding material 50, the structure being held together with stitching 46. Many types of coverings are suitable, as for example, synthetic or natural fabrics, and including such things as nylon, cotton, or others; however, fabrics having the ability to absorb perspiration, as well as softness, provide the wearer with greater comfort, and are therefore, preferred.

While padding need not be used, it provides additional comfort to the wearer, and is preferred for use with cinctures of the invention other than the palm cincture 28, which is normally made from a single layer of material. Such padding may be selected from materials as for instance rubber, polyurethane, cotton batting, and the like, foamed materials being especially useful since they provide additional softness.

FIG. 5 is a cross section of the palm portion of an individual's hand, generally 54. The Figure shows the brace crosspiece 30 folding around the ulnar side of the hand having attached thereto, a palm cincture 28. The palm cincture 28 is shown passed through buckle 34, doubled back and the VELCRO pad 42 on the end thereof secured to VELCRO pad 44. Buckle strap 38b is employed to attach the buckle 34 to the crosspiece 30. The Figure illustrates how the ulnar side of the crosspiece 30 adjacent to the wearer's little finger, is bent around the edge of the wearer's hand to prevent ulnar deviation, or bending, of the hand at the wrist, a movement which would place undesirable pressure on the carpal tunnel. Similar bending of the opposite side of the crosspiece is unneeded since the natural anatomy of the wrist prevents harmful deviation in that direction. Beside being unnecessary, bending of the opposite side of the crosspiece is undesirable since it would unnecessarily limit the desired mobility of the hand. As previously stated, one of the notable advantages of the carpal brace of the invention resides in the fact that the design of the palm cincture 28 permits the substantially free movement of the fingers and thumb, while at the same time limiting hyperextension, upper bending; flexion, downward bending; or ulnar deviation of the wrist, all of which must be inherent in the movement limitations imposed by the brace if it is to satisfactorily perform its intended functions.

FIG. 6 is a plan view of a carpal brace rigidifying member, generally 51. Member 51, which functions to provide the custom fitting, stiffening or rigidifying characteristic of the brace, comprises a spine portion 52 with the crosspiece portion 53. The spine portion 52 includes a thin, brace-reinforcing member 56, which may be a downwardly-facing, hollow, concave shaped rod fastened to the spine portion, for example, by rivets 58 or other fastening means, which contributes to the overall rigidity of the member 51. Desirably, the member 51 is made from an electrically non-conductive material, ideally plastic, and among suitable plastic materials, plastics of the thermoplastic type are strongly preferred, since the carpal brace is normally heated to the point at which its softening, or deformation temperature is reached, to permit the ulnar end of the crosspiece portion 53 to be bent over the edge of the wearer's hand, desirably customizing the fit of the brace to the wearer. Although other thermoplastic materials may be used, PVC compounds have been found particularly desirable in practicing the invention, and their use is, therefore, preferred.

FIG. 6a shows a side elevation of the carpal brace spine member of FIG. 6, generally 51, including the spine portion 52, which forms a dorsi-lift 33 in the area adjacent to the portion of the spine connecting with the crosspiece portion 53. The Figure also shows additional details of the attachment of the brace-reinforcing member 56 to the spine portion 52 by means of rivets 58. As previously stated while the angle of the dorsi-lift may vary, normally it will form an angle of from about 7 degrees to 10 degrees in the average individual.

FIG. 7 illustrates a cross section of the carpal brace rigidifying member of FIG. 6, along Line 7—7. The Figure shows the spine portion 52 of the rigidifying member 51, with a reinforcement bar 56 held to the rigidifying member by rivets 58.

While in accordance with the patent statutes, a preferred embodiment and best mode has been presented, the scope of the invention is not limited thereto, but rather is measured by the scope of the attached claims.

What is claimed is:

1. A brace for preventing or treating trauma of the carpal tunnel of an arm of a Homo sapiens, said brace comprising:

a rigid spine element, having distal and proximal ends and a middle therebetween, the length of said spine element selected so as to span the distance between the back of the Homo sapiens' hand to the proximal end of the Homo sapiens' forearm, when positioned on the dorsal surface thereof, the width of said spine element being narrow with respect to the width of said Homo sapiens' forearm;

a cross-piece element, having ulnar and radial ends and a middle therebetween, the length of said cross-piece element selected so as to at least span the back of the Homo sapiens' hand from the ulnar to the radial side thereof, said cross-piece element being affixed to or integral with the distal end of the spine element such that the cross-piece element is essentially perpendicular to the spine element and such that the point of connection of the spine element to the cross-piece element is closer to the radial end than the ulnar end thereof; and at least three cincture means for securing the brace to the arm, the first said cincture means located lengthwise on the cross-piece element so as to pass across the palm and secure the hand contiguously to the brace, the second cincture means near or at the proximal end of the spine element so as to pass around the upper forearm and secure it contiguously to the brace, and the third and any additional cincture means located at least 2¼ inches proximal to the proximal end of the carpal bones of the Homo sapiens' hand to secure such additional portion of the forearm contiguously to the brace;

said spine element further being inclined upwardly at its distal end to an angle sufficient to conform to the natural dorsi-lift of the Homo sapiens;

said brace essentially positioned on the dorsal side of the Homo sapiens' arm to prevent ulnar deviation, flexion or hyperextension of the Homo sapiens' wrist while still allowing full mobility of the fingers, thumb and elbow.

2. The brace of claim 1 wherein the ulnar end of the cross-piece element is sufficiently long to be bent around the ulnar edge of the hand of the Homo sapiens to further limit ulnar deviation of the hand.

3. The brace of claim 1 wherein the angle of inclination of the distal end of the spine element is in the range of about 7 to about 10 degrees.

4. The brace of claim 1 wherein the cincture means are straps fastened by cooperating hooks and loops sold under the trademark "VELCRO".

5. The brace of claim 1 wherein the spine element and cross-piece element are fabricated from a thermoplastic material.

6. The brace of claim 1 wherein the spine element and cross-piece element are covered with a fabric material.

7. The brace of claim 6 wherein padding is interposed between the spine and cross-piece elements and the fabric covering.

8. The method of preventing or treating trauma of the carpal tunnel of an arm of a Homo sapiens, said method comprising:

providing a brace comprising a rigid spine element, having distal and proximal ends and a middle therebetween, the length of said spine element selected so as to span the distance between the back of the Homo sapiens' hand to the proximal end of the Homo sapiens' forearm, when positioned on the dorsal surface thereof, the width of said spine element being narrow with respect to the width of said Homo sapiens' forearm; a cross-piece element, having ulnar and radial ends and a middle therebetween, the length of said cross-piece element selected so as to at least span the back of the Homo sapiens's hand from the ulnar to the radial side thereof, said cross-piece element being affixed to or integral with the distal end of the spine element such that the cross-piece element is essentially perpendicular to the spine element and such that the point of connection of the spine element to the cross-piece element is closer to the radial end than the ulnar end thereof; and at least three cincture means for securing the brace to the arm, the first said cincture means located lengthwise on the cross-piece element so as to pass across the palm and secure the hand contiguously to the brace, the second cincture means near or at the proximal end of the spine element so as to pass around the upper forearm and secure it contiguously to the brace, and the third and any additional cincture means located at least 2¼ inches proximal to the proximal end of the carpal bones of the Homo sapiens' hand to secure such additional portion of the forearm contiguously to the brace; said spine element further being inclined upwardly at its distal end to an angle sufficient to conform to the natural dorsi-lift of the Homo sapiens; said brace essentially positionable on the dorsal side of the Homo sapiens' arm to prevent ulnar deviation, flexion or hyperextension of the Homo sapiens' wrist while still allowing full mobility of the fingers, thumb and elbow;

further limiting ulnar deviation of the hand by bending the ulnar end of said cross-piece element around the ulnar edge of said hand; placing said brace on the dorsal surface of the hand and forearm of the Homo sapiens; and firmly securing the brace onto the dorsal surface of said forearm and hand by the said cincture means.

* * * * *